(12) United States Patent
Jumper et al.

(10) Patent No.: US 12,100,477 B2
(45) Date of Patent: Sep. 24, 2024

(54) PROTEIN STRUCTURE PREDICTION FROM AMINO ACID SEQUENCES USING SELF-ATTENTION NEURAL NETWORKS

(71) Applicant: DeepMind Technologies Limited, London (GB)

(72) Inventors: John Jumper, London (GB); Andrew W. Senior, London (GB); Richard Andrew Evans, London (GB); Russell James Bates, London (GB); Mikhail Figurnov, London (GB); Alexander Pritzel, London (GB); Timothy Frederick Goldie Green, London (GB)

(73) Assignee: DeepMind Technologies Limited, London (GB)

( * ) Notice: Subject to any disclaimer, the term of this patent is extended or adjusted under 35 U.S.C. 154(b) by 572 days.

(21) Appl. No.: 17/108,890

(22) Filed: Dec. 1, 2020

(65) Prior Publication Data
US 2021/0166779 A1 Jun. 3, 2021

Related U.S. Application Data

(60) Provisional application No. 62/942,688, filed on Dec. 2, 2019.

(51) Int. Cl.
*G16B 15/00* (2019.01)
*G06N 3/02* (2006.01)

(52) U.S. Cl.
CPC .............. *G16B 15/00* (2019.02); *G06N 3/02* (2013.01)

(58) Field of Classification Search
USPC .......................................................... 702/19
See application file for complete search history.

(56) References Cited

U.S. PATENT DOCUMENTS 5,958,784 A 9/1999 Benner

OTHER PUBLICATIONS

Shin, Bonggun, et al. "Self-attention based molecule representation for predicting drug-target interaction." Machine Learning for Healthcare Conference. PMLR, 2019. (Year: 2019).*
DeepDTA (2020) About DeepDTA: deep drug-target binding affinity prediction, GitHub. Available at: https://github.com/hkmztrk/DeepDTA/ (Accessed: May 29, 2023). (Year: 2020).*
Karimi, Mostafa, et al. "DeepAffinity: interpretable deep learning of compound-protein affinity through unified recurrent and convolutional neural networks." Bioinformatics 35.18 (2019): 3329-3338. (Year: 2019).*
Bepler, Tristan, and Bonnie Berger. "Learning protein sequence embeddings using information from structure." arXiv preprint arXiv:1902.08661 (2019). (Year: 2019).*
Peters, Matthew. "Deep contextualized word representations." arXiv preprint arXiv:1802.05365 (2018). (Year: 2018).*
International Preliminary Report on Patentability in International Appln. No. PCT/EP2020/084238, dated May 17, 2022, 11 pages.
Defay et al., "Evaluation of Current Techniques for Ab Initio Protein Structure Prediction," PROTEINS: Structure, Function, and Genetics, 1995, 23:431-445.
Knighton et al., "Crystal Structure of the Catalytic Subunit of Cyclic Adenosine Monophosphate-Dependent Protein Kinase," Science, Jul. 1991, 253:5018:407-414.
Lei Ba et al., "Layer Normalization," CoRR, Jul. 2016, arXiv:1607.06450, 14 pages.
Prodromou et al., "Identification and Structural Characterization of the ATP/ADP-Binding Site in the Hsp90 Molecular Chaperone," Cell, Jul. 1991, 90:65-75.
Thornton et al., "Prediction of Progress at Least," Nature, Nov. 1991, 354:105-106.
Fan et al., "Virtual Ligand Screening Against Comparative Protein Structure Models," Computational Drug Discovery and Design, Nov. 2011, pp. 105-126.
Mirabello et al., "rawMSA: End-to-end Deep Learning using raw Multiple Sequence Alignments," PLOS ONE, Aug. 2019, 14(8):e0220182.
PCT International Search Report and Written Opinion in International Appln. No. PCT/EP2020/084238, dated Feb. 23, 2021, 17 pages.
Vaswani et al., "Attention Is All You Need," 31st Conference on Neural Information Processing Systems, Jun. 2017, 15 pages.
[No Author Listed], "Protein Data Bank: the single global archive for 3D macromolecular structure data," Nucleic Acids Res., Jan. 8, 2019, 47(D1):D520-D528.
Abriata et al., "A further leap of improvement in tertiary structure prediction in CASP13 prompts new routes for future assessments," Proteins, Jul. 25, 2019, 87:1100-1112.
Alley et al., "Unified rational protein engineering with sequence-based deep representation learning," Nat. Methods, Oct. 21, 2019,16(12):1315-1322.
AlQuraishi, "End-to-end differentiable learning of protein structure," Cell Syst., Apr. 24, 2019, 8:292-301.
Altschuh et al., "Correlation of co-ordinated amino acid substitutions with function in viruses related to tobacco mosaic virus," J. Mol. Biol., Feb. 20, 1987, 193(4):693-707.
Anfinsen et al., "Principles that govern the folding of protein chains," Science, Jul. 20, 1973, 181(4096):223-230.
Ashish et al., "TensorFlow: large-scale machine learning on heterogeneous systems," CoRR, Mar. 14, 2016, arxiv.org/abs/1603.04467, 19 pages.

(Continued)

*Primary Examiner* — G. Steven Vanni
(74) *Attorney, Agent, or Firm* — Fish & Richardson P.C.

(57) ABSTRACT

Methods, systems, and apparatus, including computer programs encoded on a computer storage medium, for determining a predicted structure of a protein that is specified by an amino acid sequence. In one aspect, a method comprises: obtaining a multiple sequence alignment for the protein; determining, from the multiple sequence alignment and for each pair of amino acids in the amino acid sequence of the protein, a respective initial embedding of the pair of amino acids; processing the initial embeddings of the pairs of amino acids using a pair embedding neural network comprising a plurality of self-attention neural network layers to generate a final embedding of each pair of amino acids; and determining the predicted structure of the protein based on the final embedding of each pair of amino acids.

20 Claims, 5 Drawing Sheets

(56) References Cited

OTHER PUBLICATIONS

Bai et al., "How cryo-EM is revolutionizing structural biology," Trends Biochem. Sci., Nov. 7, 2014, 40:49-57.

Carreira et al., "Human pose estimation with iterative error feedback," Proc. IEEE Conference on Computer Vision and Pattern Recognition, 2016, pp. 4733-4742.

Deepmind.google [online], "Open sourcing Sonnet—a new library for constructing neural networks," Apr. 7, 2017, retrieved on Jan. 19, 2024, retrieved from URL<https://deepmind.google/discover/blog/open-sourcing-sonnet-a-new-library-for-constructing-neural-networks/>, 4 pages.

Deorowicz et al., "FAMSA: fast and accurate multiple sequence alignment of huge protein families," Sci. Rep., Sep. 27, 2016, 6:33964.

Devlin et al., "BERT: pre-training of deep bidirectional transformers for language understanding," CoRR, Oct. 11, 2018, arxiv.org/abs/1810.04805, 16 pages.

Dill et al., "The protein folding problem," Annu. Rev. Biophys., Jun. 9, 2008, 37:289-316.

Eastman et al., "OpenMM 7: rapid development of high performance algorithms for molecular dynamics," Plos Comput. Biol., Jul. 26, 2017, 13(7):e1005659.

Eddy, "Accelerated profile HMM searches," Plos Comput. Biol., Oct. 20, 2011, 7(10):e1002195.

ElGamacy et al., "An interface-driven design strategy yields a novel, corrugated protein architecture," ACS Synth. Biol., Aug. 27, 2018, 7(9):2226-2235.

Fariselli et al., "Prediction of contact maps with neural networks and correlated mutations," Protein Engineering, Design and Selection, Nov. 2001, 14(11):835-843.

He et al., "Deep residual learning for image recognition," Proc, Proceedings of the IEEE Conference on Computer Vision and Pattern Recognition, 2016, pp. 770-778.

Hornak et al., "Comparison of multiple Amber force fields and development of improved protein backbone parameters," Proteins, Sep. 15, 2006, 65(3):7120-725.

Huang et al., "CCNet: criss-cross attention for semantic segmentation," CoRR, Nov. 28, 2018, arxiv.org/abs/1811.11721, 13 pages.

Ingraham et al., "Generative models for graph-based protein design," ICLR, May 3, 2019, 10 pages.

Ingraham et al., "Learning protein structure with a differentiable simulator," ICLR, Dec. 20, 2018, 24 pages.

Jaskolski et al., "A brief history of macromolecular crystallography, illustrated by a family tree and its Nobel fruits," Febs J., Apr. 3, 2014, 281:3985-4009.

Johnson et al., "Hidden Markov model speed heuristic and iterative HMM search procedure," BMC Bioinformatics, Aug. 18, 2010, 11:431.

Jones et al., "PSICOV: precise structural contact prediction using sparse inverse covariance estimation on large multiple sequence alignments," Bioinformatics, Jan. 2012, 28(2):184-190.

Kryshtafovych et al., "Critical assessment of methods of protein structure prediction (CASP)—round XIII," Proteins, Oct. 7, 2019, 87(12):1011-1020.

Kuhlman et al., "Advances in protein structure prediction and design," Nat. Rev. Mol. Cell Biol., Nov. 2019, 20(11):681-697.

Li, "Universal transforming geometric network," CoRR, Aug. 2, 2019, arxiv.org/abs/1908.00723, 11 pages.

Mariani et al., "IDDT: a local superposition-free score for comparing protein structures and models using distance difference tests," Bioinformatics, Nov. 2013, 29(21):2722-2728.

Marks et al., "Protein 3D structure computed from evolutionary sequence variation," PloS One, Dec. 7, 2011, 6(12):e28766.

Marks et al., "Protein structure prediction from sequence variation," Nat. Biotechnol., Nov. 2012, 30(11):1072-1080.

Mirdita et al., "Uniclust databases of clustered and deeply annotated protein sequences and alignments," Nucleic Acids Res., Nov. 29, 2016, 45(D1):D170-D176.

Moult et al., "A large-scale experiment to assess protein structure prediction methods," Proteins, Nov. 1995, 23(3):ii-iv.

Qian et al., "Predicting the secondary structure of globular proteins using neural network models," J. Mol. Biol., Aug. 20, 1988, 202(4):865-884.

Remmert et al., "HHblits: lightning-fast iterative protein sequence searching by HMM-HMM alignment," Nat. Methods, Feb. 2012, 9(2):173-175.

Roy et al., "I-TASSER: a unified platform for automated protein structure and function prediction," Nat. Protocols, Mar. 25, 2010, 5:725-738.

Šali et al., "Comparative protein modelling by satisfaction of spatial restraints," J. Mol. Biol., Dec. 5, 1993, 234(3):779-815.

Senior et al., "Protein structure prediction using multiple deep neural networks in the13th Critical Assessment of Protein Structure Prediction (CASP13)," Proteins, Sep. 27, 2019, 87(12):1141-1148.

Shindyalov et al., "Can three-dimensional contacts in protein structures be predicted by analysis of correlated mutations?," Protein Engineering, Design and Selection, Mar. 1994, 7(3):349-358.

Sippl, "Calculation of conformational ensembles from potentials of mean force: An approach to the knowledge-based prediction of local structures in globular proteins," J. Mol. Biol., Jun. 20, 1990, 213:859-883.

Steinegger et al., "Clustering huge protein sequence sets in linear time," Nat. Commun., 2018, 9:2542.

Steinegger et al., "HH-suite3 for fast remote homology detection and deep protein annotation," BMC Bioinformatics, Sep. 14, 2019, 20:473.

Steinegger et al., "MMseqs2 enables sensitive protein sequence searching for the analysis of massive data sets," Nat. Biotechnol., Oct. 16, 2017, 35(11):1026-1028.

Steinegger et al., "Protein-level assembly increases protein sequence recovery from metagenomic samples manyfold," Nat. Methods, Jul. 2019, 16:603-606.

Suzek et al., "UniRef clusters: a comprehensive and scalable alternative for improving sequence similarity searches," Bioinformatics, Mar. 2015, 31(6):926-932.

Tensorflow.org [online], "XLA," Nov. 5, 2018, retrieved on Jan. 19, 2024, retrieved from URL<https://deepmind.google/discover/blog/open-sourcing-sonnet-a-new-library-for-constructing-neural-networks/>, 4 pages.

Tu et al., "Auto-context and its application to high-level vision tasks and 3D brain image segmentation," IEEE Trans. Pattern Anal. Mach. Intell., Oct. 2010, 32(10):1744-1757.

Wang et al., "Accurate de novo prediction of protein contact map by ultra-deep learning model," Plos Comput. Biol., Jan. 5, 2017, 13:e1005324.

Weigt et al., "Identification of direct residue contacts in protein-protein interaction by message passing," Proc. Natl Acad. Sci., Jan. 6, 2009, 106(1):67-72.

Wu et al., "Analysis of several key factors influencing deep learning-based inter-residue contact prediction," Bioinformatics, Aug. 30, 2019, 36:1091-1098.

Wüthrich, "The way to NMR structures of proteins," Nat. Struct. Biol., Nov. 2001, 8:923-925.

Zemla, "LGA: a method for finding 3D similarities in protein structures," Nucleic Acids Res., Jul. 1, 2003, 31(13):3370-3374.

Zhang et al., "Scoring function for automated assessment of protein structure template quality," Proteins, Oct. 8, 2004, 57(4):702-710.

Zheng et al., "Deep-learning contact-map guided protein structure prediction in CASP13," Proteins, Jul. 31, 2019, 87:1149-1164.

\* cited by examiner

PROTEIN STRUCTURE PREDICTION FROM AMINO ACID SEQUENCES USING SELF-ATTENTION NEURAL NETWORKS

BACKGROUND

This specification relates to predicting protein structures.

A protein is specified by a sequence of amino acids. An amino acid is an organic compound which includes an amino functional group and a carboxyl functional group, as well as a side-chain (i.e., group of atoms) that is specific to the amino acid. Protein folding refers to a physical process by which a sequence of amino acids folds into a three-dimensional configuration. The structure of a protein defines the three-dimensional configuration of the atoms in the amino acid sequence of the protein after the protein undergoes protein folding. When in a sequence linked by peptide bonds, the amino acids may be referred to as amino acid residues.

Predictions can be made using machine learning models. Machine learning models receive an input and generate an output, e.g., a predicted output, based on the received input. Some machine learning models are parametric models and generate the output based on the received input and on values of the parameters of the model. The structure of a protein may be predicted based on the amino acid sequence that specifies the protein.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that performs protein structure prediction.

According to a first aspect there is provided a method performed by one or more data processing apparatus for determining a predicted structure of a protein that is specified by an amino acid sequence. The method comprises obtaining a multiple sequence alignment (MSA) for the protein. The method may further comprise determining, from the multiple sequence alignment and for each pair of amino acids in the amino acid sequence of the protein, a respective initial embedding of the pair of amino acids. The method may further comprise processing the initial embeddings of the pairs of amino acids using a pair embedding neural network comprising a plurality of self-attention neural network layers to generate a final embedding of each pair of amino acids. The method may then comprise determining the predicted structure of the protein based on the final embedding of each pair of amino acids.

Some advantages of the method are described later. For example implementations of the method generate "pair" embeddings which encode relationships between pairs of amino acids in the protein. (For example, the pair embedding for a pair of amino acids in the protein can encode a relationship between respective specified atoms, e.g., carbon alpha atoms, in the pair of amino acids). These may then be processed by subsequent neural network layers to determine additional information, in particular the predicted structure of the protein. In implementations a folding neural network processes the pair embeddings to determine the predicted structure, e.g., in terms of structure parameters such as atomic coordinates for carbon atoms of the protein or backbone torsion angles. Example implementations of such a folding neural network are described later, but others may be used. In some implementations the final pair embedding is used to determine an initial embedding of each (single) amino acid in the amino acid sequence, and this single embedding may be used alone or in conjunction with the pair embedding to determine the predicted structure.

In implementations each self-attention neural network layer receives a current embedding of each pair of amino acids and updates the current embedding using attention over the current embeddings of the pairs of amino acids or over a proper subset of these. For example the self-attention neural network layer may determine set of attention weights which are applied to the current embeddings (or subset) to update the current embedding e.g. based on an attention weighted sum of the current embeddings.

In some implementations the current embeddings of the pairs of amino acids are arranged into a two-dimensional array. The self-attention neural network layers may then comprise row-wise and/or column-wise self-attention neural network layers e.g. an alternating sequence. A row-(or column-) wise self-attention neural network layer may update the current embedding of the pair of amino acids using attention over only current embeddings of pairs of amino acids that are located in a same row (or column) as the current embedding of the pair of amino acids.

Using self-attention has been found to significantly improve the accuracy of predicted structures, e.g., by generating embeddings which are more easily processed to determine predicted structure parameters. Row- and column-wise processing helps to achieve this with reduced computational resources.

The initial embedding of each pair of amino acids may be determined by partitioning the MSA into a set of cluster amino acid sequences and a (larger) set of extra amino acid sequences. An embedding of each set may then be generated and the embedding of the cluster amino acid sequences may be updated using the embedding of the extra amino acid sequences. The updated embedding of the cluster amino acid sequences may then be used to determine the initial embeddings of the pairs of amino acids. In this way a large set of extra amino acid sequences may be used to enrich the information in embeddings of a smaller set of amino acid sequences (the cluster amino acid sequences), for computational efficiency. The processing may be performed by a cross-attention neural network. The cross-attention neural network may comprise a neural network which uses attention over (i.e. attention weights applied to) the embedding of the extra amino acid sequences to update the embedding of the cluster amino acid sequences. Optionally the process may also involve updating the embedding of the extra amino acid sequences using attention over the embedding of the cluster amino acid sequences. The updating of the embeddings of the cluster amino acid sequences, and optionally of the extra amino acid sequences, may be performed repeatedly e.g. sequentially in time or using sequential neural network layers.

In a second aspect there is provided a system including: one or more computers; and one or more storage devices communicatively coupled to the one or more computers, where the one or more storage devices store instructions that, when executed by the one or more computers, cause the one or more computers to perform operations including the operations of the method of the first aspect.

In a third aspect there are provided one or more non-transitory computer storage media storing instructions that, when executed by one or more computers, cause the one or more computers to perform operations including the operations of the method of the first aspect.

The methods and systems described herein may be used to obtain a ligand such as a drug or a ligand of an industrial enzyme. For example, a method of obtaining a ligand may include obtaining a target amino acid sequence, in particular the amino acid sequence of a target protein, and performing a computer-implemented method as described above or herein, using the target amino acid sequence as the sequence of amino acids, to determine a (tertiary) structure of the target protein, i.e., the predicted protein structure. The method may then include evaluating an interaction of one or more candidate ligands with the structure of the target protein. The method may further include selecting one or more of the candidate ligands as the ligand dependent on a result of the evaluating of the interaction.

In some implementations, evaluating the interaction may include evaluating binding of the candidate ligand with the structure of the target protein. For example, evaluating the interaction may include identifying a ligand that binds with sufficient affinity for a biological effect. In some other implementations, evaluating the interaction may include evaluating an association of the candidate ligand with the structure of the target protein which has an effect on a function of the target protein, e.g., an enzyme. The evaluating may include evaluating an affinity between the candidate ligand and the structure of the target protein, or evaluating a selectivity of the interaction.

The candidate ligand(s) may be derived from a database of candidate ligands, and/or may be derived by modifying ligands in a database of candidate ligands, e.g., by modifying a structure or amino acid sequence of a candidate ligand, and/or may be derived by stepwise or iterative assembly/optimization of a candidate ligand.

The evaluation of the interaction of a candidate ligand with the structure of the target protein may be performed using a computer-aided approach in which graphical models of the candidate ligand and target protein structure are displayed for user-manipulation, and/or the evaluation may be performed partially or completely automatically, for example using standard molecular (protein-ligand) docking software. In some implementations the evaluation may include determining an interaction score for the candidate ligand, where the interaction score includes a measure of an interaction between the candidate ligand and the target protein. The interaction score may be dependent upon a strength and/or specificity of the interaction, e.g., a score dependent on binding free energy. A candidate ligand may be selected dependent upon its score.

In some implementations the target protein includes a receptor or enzyme and the ligand is an agonist or antagonist of the receptor or enzyme. In some implementations the method may be used to identify the structure of a cell surface marker. This may then be used to identify a ligand, e.g., an antibody or a label such as a fluorescent label, which binds to the cell surface marker. This may be used to identify and/or treat cancerous cells.

In some implementations the candidate ligand(s) may include small molecule ligands, e.g., organic compounds with a molecular weight of <900 daltons. In some other implementations the candidate ligand(s) may include polypeptide ligands, i.e., defined by an amino acid sequence.

Some implementations of the method may be used to determine the structure of a candidate polypeptide ligand, e.g., a drug or a ligand of an industrial enzyme. The interaction of this with a target protein structure may then be evaluated; the target protein structure may have been determined using a computer-implemented method as described herein or using conventional physical investigation techniques such as x-ray crystallography and/or magnetic resonance techniques.

Thus in another aspect there is provided a method of obtaining a polypeptide ligand (e.g., the molecule or its sequence). The method may include obtaining an amino acid sequence of one or more candidate polypeptide ligands. The method may further include performing a computer-implemented method as described above or herein, using the amino acid sequence of the candidate polypeptide ligand as the sequence of amino acids, to determine a (tertiary) structure of the candidate polypeptide ligand. The method may further include obtaining a target protein structure of a target protein, in silico and/or by physical investigation, and evaluating an interaction between the structure of each of the one or more candidate polypeptide ligands and the target protein structure. The method may further include selecting one or more of the candidate polypeptide ligands as the polypeptide ligand dependent on a result of the evaluation.

As before evaluating the interaction may include evaluating binding of the candidate polypeptide ligand with the structure of the target protein, e.g., identifying a ligand that binds with sufficient affinity for a biological effect, and/or evaluating an association of the candidate polypeptide ligand with the structure of the target protein which has an effect on a function of the target protein, e.g., an enzyme, and/or evaluating an affinity between the candidate polypeptide ligand and the structure of the target protein, or evaluating a selectivity of the interaction. In some implementations the polypeptide ligand may be an aptamer.

Implementations of the method may further include synthesizing, i.e., making, the small molecule or polypeptide ligand. The ligand may be synthesized by any conventional chemical techniques and/or may already be available, e.g., may be from a compound library or may have been synthesized using combinatorial chemistry.

The method may further include testing the ligand for biological activity in vitro and/or in vivo. For example the ligand may be tested for ADME (absorption, distribution, metabolism, excretion) and/or toxicological properties, to screen out unsuitable ligands. The testing may include, e.g., bringing the candidate small molecule or polypeptide ligand into contact with the target protein and measuring a change in expression or activity of the protein.

In some implementations a candidate (polypeptide) ligand may include: an isolated antibody, a fragment of an isolated antibody, a single variable domain antibody, a bi- or multi-specific antibody, a multivalent antibody, a dual variable domain antibody, an immuno-conjugate, a fibronectin molecule, an adnectin, an DARPin, an avimer, an affibody, an anticalin, an affilin, a protein epitope mimetic or combinations thereof. A candidate (polypeptide) ligand may include an antibody with a mutated or chemically modified amino acid Fc region, e.g., which prevents or decreases ADCC (antibody-dependent cellular cytotoxicity) activity and/or increases half-life when compared with a wild type Fc region.

Misfolded proteins are associated with a number of diseases. Thus in a further aspect there is provided a method of identifying the presence of a protein mis-folding disease. The method may include obtaining an amino acid sequence of a protein and performing a computer-implemented method as described above or herein using the amino acid sequence of the protein to determine a structure of the protein. The method may further include obtaining a structure of a version of the protein obtained from a human or animal body, e.g., by conventional (physical) methods. The method may then include comparing the structure of the protein with the structure of the version obtained from the body and identifying the presence of a protein mis-folding disease dependent upon a result of the comparison. That is, mis-folding of the version of the protein from the body may be determined by comparison with the in silico determined structure.

In some other aspects a computer-implemented method as described above or herein may be used to identify active/binding/blocking sites on a target protein from its amino acid sequence.

Particular embodiments of the subject matter described in this specification can be implemented so as to realize one or more of the following advantages.

The protein structure prediction system described in this specification can predict the structure of a protein by a single forward pass through a collection of jointly trained neural networks, which may take less than one second. In contrast, some conventional systems predict the structure of a protein by an extended search process through the space of possible protein structures to optimize a scalar score function, e.g., using simulated annealing or gradient descent techniques. Such a search process may require millions of search iterations and consume hundreds of central processing unit (CPU) hours. Predicting protein structures by a single forward pass through a collection of neural networks may enable the structure prediction system described in this specification to consume fewer computational resources (e.g., memory and computing power) than systems that predict protein structures by an iterative search process. Moreover, the structure prediction system described in this specification can (in some cases) predict protein structures with an accuracy comparable to or higher than that of more computationally intensive structure prediction systems.

To generate a predicted protein structure, the structure prediction system described in this specification generates a collection of embeddings representing the protein by processing a multiple sequence alignment (MSA) corresponding to the protein using learned operations implemented by neural network layers. In contrast, some conventional systems rely on generating MSA features by hand-crafted feature engineering techniques. Processing the MSA using learned neural network operations rather than hand-crafted feature engineering techniques may enable the structure prediction system described in this specification to predict protein structures more accurately than some conventional systems.

The structure prediction system described in this specification processes an MSA to generate a collection of "pair" embeddings, where each pair embedding corresponds to a respective pair of amino acids in the protein. The system then enriches the pair embeddings by processing them through a sequence of self-attention neural network layers, and uses the enriched pair embeddings to predict the protein structure. Generating and enriching the pair embeddings enables the structure prediction system to develop an effective representation of the relationships between pairs of amino acids in the protein, thereby facilitating accurate protein structure prediction. In contrast, some conventional systems rely on "single" embeddings (i.e., that each correspond to a respective amino acid, rather than a pair of amino acids), which may be less effective for developing effective representations for protein structure prediction. Using pair embeddings may enable the structure prediction system described in this specification to predict protein structures more accurately than it otherwise would.

The structure of a protein determines the biological function of the protein. Therefore, determining protein structures may facilitate understanding life processes (e.g., including the mechanisms of many diseases) and designing proteins (e.g., as drugs, or as enzymes for industrial processes). For example, which molecules (e.g., drugs) will bind to a protein (and where the binding will occur) depends on the structure of the protein. Since the effectiveness of drugs can be influenced by the degree to which they bind to proteins (e.g., in the blood), determining the structures of different proteins may be an important aspect of drug development. However, determining protein structures using physical experiments (e.g., by x-ray crystallography) can be time-consuming and very expensive. Therefore, the protein prediction system described in this specification may facilitate areas of biochemical research and engineering which involve proteins (e.g., drug development).

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a structure prediction system for predicting the structure of a protein, that is, for predicting the three-dimensional configuration of the sequence of amino acids in the protein after the protein undergoes protein folding.

To predict the structure of a protein, the structure prediction system processes a multiple sequence alignment (MSA) corresponding to the protein to generate a representation of the protein as a collection of "pair" embeddings. Each pair embedding corresponds to pair of amino acids in the protein, and the structure prediction system enriches the pair embeddings by repeatedly updating them using a sequence of self-attention neural network layers that share information between the pair embeddings.

The structure prediction system processes the pair embeddings to generate a respective "single" embedding of each amino acid in the protein, and processes the single embeddings using a folding neural network to generate the predicted structure of the protein. The predicted structure of the protein may be defined by a set of structure parameters that define a spatial location and optionally also a rotation of each amino acid in the protein.

These features and other features are described in more detail below.

Figure 1:
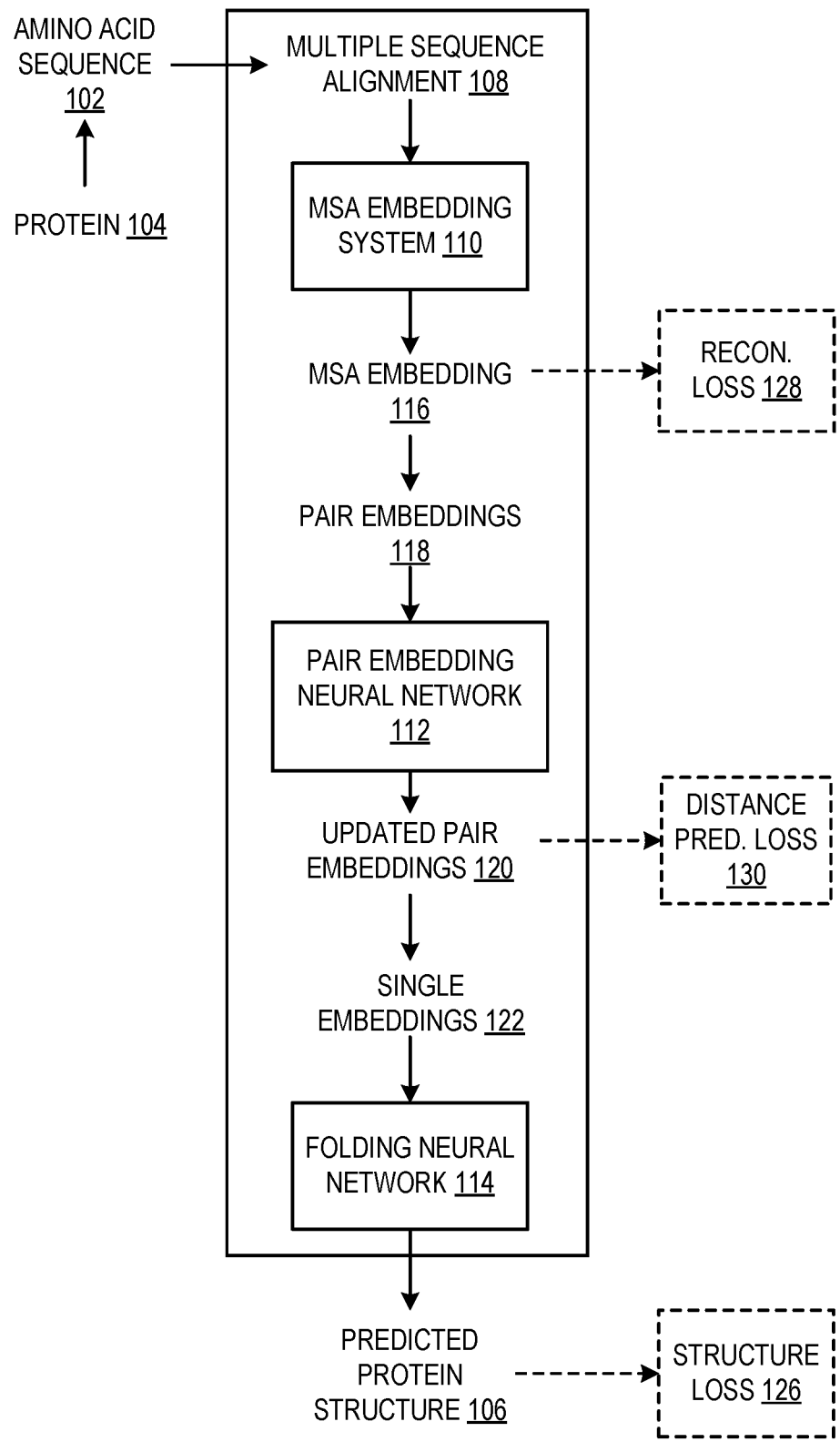
FIG. 1 shows an example protein structure prediction system.

FIG. 1 shows an example protein structure prediction system 100. The protein structure prediction system 100 is an example of a system implemented as computer programs on one or more computers in one or more locations in which the systems, components, and techniques described below are implemented.

The structure prediction system 100 is configured to process data defining an amino acid sequence 102 of a protein 104 to generate a predicted structure 106 of the protein 104. Each amino acid in the amino acid sequence 102 is an organic compound which includes an amino functional group and a carboxyl functional group, as well as a side-chain (i.e., group of atoms) which is specific to the amino acid. The predicted structure 106 defines an estimate of a three-dimensional (3-D) configuration of the atoms in the amino acid sequence 102 of the protein 104 after the protein 104 undergoes protein folding.

As used throughout this specification, the term "protein" may be understood to refer to any biological molecule that is specified by one or more sequences of amino acids. For example, the term protein may be understood to refer to a protein domain (i.e., a portion of an amino acid sequence that can undergo protein folding nearly independently of the rest of the amino acid sequence) or a protein complex (i.e., that is specified by multiple associated amino acid sequences).

The amino acid sequence 102 can be represented in any appropriate numerical format. For example, the amino acid sequence 102 may be represented as a sequence of one-hot vectors. In this example, each one-hot vector represents a corresponding amino acid in the amino acid sequence 102. A one-hot vector has a different component for each different amino acid (e.g., of a predetermined number of amino acids e.g. 21). A one-hot vector representing a particular amino acid has value one (or some other predetermined value) in the component corresponding to the particular amino acid and value zero (or some other predetermined value) in the other components.

The predicted structure 106 of the protein 104 is defined by the values of a set of structure parameters. The set of structure parameters may include: (i) location parameters, and (ii) rotation parameters, for each amino acid in the protein 104.

The location parameters for an amino acid may specify a predicted 3-D spatial location of a specified atom in the amino acid in the structure of the protein. The specified atom may be the alpha carbon atom in the amino acid, i.e., the carbon atom in the amino acid to which the amino functional group, the carboxyl functional group, and the side-chain are bonded. The location parameters for an amino acid may be represented in any appropriate coordinate system, e.g., a three-dimensional [x, y, z] Cartesian coordinate system.

The rotation parameters for an amino acid may specify the predicted "orientation" of the amino acid in the structure of the protein. More specifically, the rotation parameters may specify a 3-D spatial rotation operation that, if applied to the coordinate system of the location parameters, causes the three "main chain" atoms in the amino acid to assume fixed positions relative to the rotated coordinate system. The three main chain atoms in the amino acid refer to the linked series of nitrogen, alpha carbon, and carbonyl carbon atoms in the amino acid (or, e.g., the alpha carbon, nitrogen, and oxygen atoms in the amino acid). The rotation parameters for an amino acid may be represented, e.g., as an orthonormal 3×3 matrix with determinant equal to 1.

Generally, the location and rotation parameters for an amino acid define an egocentric reference frame for the amino acid. In this reference frame, the side-chain for each amino acid may start at the origin, and the first bond along the side-chain (i.e., the alpha carbon-beta carbon bond) may be along a defined direction.

To generate the predicted structure 106, the structure prediction system 100 obtains a multiple sequence alignment (MSA) 108 corresponding to the amino acid sequence 102 of the protein 104. The MSA 108 specifies a sequence alignment of the amino acid sequence 102 with multiple additional amino acid sequences, e.g., from other e.g. homologous proteins. The MSA 108 may be generated, e.g., by processing a database of amino acid sequences using any appropriate computational sequence alignment technique, e.g., progressive alignment construction. The amino acid sequences in the MSA 108 may be understood as having an evolutionary relationship, e.g., where each amino acid sequence in the MSA 108 may share a common ancestor. The correlations between the amino acid sequences in the MSA 108 may encode information that is relevant to predicting the structure of the protein 104. The MSA 108 may use be the same one-hot encoding as the amino acid sequence with an additional category for an insertion (or deletion) of an amino acid residue.

The structure prediction system 100 generates the predicted structure 106 from the amino acid sequence 102 and the MSA 108 using: (1) a multiple sequence alignment embedding system 110 (i.e., "MSA embedding system"), (2) a pair embedding neural network 112, and (3) a folding neural network 114, which will each be described in more detail next. As used herein, an "embedding" may be an ordered collection of numerical values, e.g., a vector or matrix of numerical values.

The MSA embedding system 110 is configured to process the MSA 108 to generate an MSA embedding 116. The MSA embedding 116 is an alternative representation of the MSA 108 that includes a respective embedding corresponding to each amino acid in each amino acid sequence of the MSA 108. The MSA embedding may be represented as a matrix with dimensionality M×N×E, where M is the number of sequences in the MSA 108, N is the number of amino acids in each amino acid sequence in the MSA 108 (which may be the same as the length of the amino acid sequence), and E is the dimensionality of the embedding corresponding to each amino acid of the MSA 108.

In one example, the MSA embedding system 110 may generate the MSA embedding M as:

$$M = h_\theta(\mathbb{I}_{AA}) \oplus h_\phi(\mathbb{I}_{MSA}) \quad (1)$$

where $\mathbb{I}_{AA}$ is a representation of the amino acid sequence 102 as a 1-D array of one-hot amino acid embedding vectors, $h_\theta(\cdot)$ is a learned linear projection operation that is applied to each embedding of the 1-D array $\mathbb{I}_{AA}$, $\mathbb{I}_{MSA}$ is a representation of the MSA 108 as a 2-D array of one-hot amino acid embedding vectors (where each row of the 2-D array corresponds to a respective amino acid sequence of the MSA), $h_\phi(\cdot)$ is a learned linear projection operation that is applied to each embedding of the 2-D array $\mathbb{I}_{MSA}$, and the $\oplus$ operation denotes adding $h_\theta(\mathbb{I}_{AA})$ to each row of $h_\phi(\mathbb{I}_{MSA})$.

Another example of an MSA embedding system 110 is described in more detail with reference to FIG. 3. The MSA embedding system 110 described with reference to FIG. 3 may generate an embedding corresponding to only a proper subset of the sequences in the MSA 108, e.g., to reduce computational resource consumption. Moreover, the MSA embedding system 110 described with reference to FIG. 3 may "share" information within and between amino sequences in the MSA 108 using self-attention neural network layers, thereby generating a more informative MSA embedding 116 that may facilitate more effective prediction of the protein structure 106.

After generating the MSA embedding 116, the structure prediction system 100 transforms the MSA embedding 116 into an alternative representation as a collection of pair embeddings 118. Each pair embedding 118 corresponds to a pair of amino acids in the amino acid sequence 102 of the protein. A pair of amino acids in the amino acid sequence 102 refers to a first amino acid and a second amino acid in the amino acid sequence 102, and the set of possible pairs of amino acids is given by:

$$\{(A_i, A_j) : 1 \leq i, j \leq N\} \quad (2)$$

where N is the number of amino acids in the amino acid sequence 102, i.e., the length of the amino acid sequence 102, $A_i$ is the amino acid at position i in the amino acid sequence 102, $A_j$ is the amino acid at position j in the sequence, and N is the number of amino acids in the amino acid sequence 102 (i.e., the length of the amino acid sequence 102). The collection of pair embeddings 118 may be represented as a matrix with dimensionality N×N×F, where N is the number of amino acids in the amino acid sequence 102 and F is the dimensionality of each pair embedding 118.

The structure prediction system 100 may generate the pair embeddings 118 from the MSA embedding 116, e.g., by computing the outer-product of the MSA embedding 116 with itself, marginalizing (e.g., averaging) out the MSA dimension of the outer product, and combining the embedding dimensions of the outer product. For example, the pair embeddings 118 may be generated as:

$$L_{mlc} = M_{mlo} \overline{L}_{oc} \quad (3)$$

$$R_{mrd} = M_{mro} \overline{R}_{od} \quad (4)$$

$$P_{lre} = L_{mlc} R_{mrd} \overline{C}_{cde} \quad (5)$$

where M denotes the MSA embedding 116 (e.g., having a first dimension indexing the sequences in the MSA, a second dimension indexing the amino acids in each sequence in the MSA, and a third dimension indexing the channels of the embedding of each amino acid), $\overline{L}$ denotes a weight matrix that multiplies M to generate the "left"-encoded embeddings L, $\overline{R}$ denotes a weight matrix that multiplies M to generate the "right"-encoded embeddings R, $\overline{C}$ denotes a weight matrix that combines the left-encoded and right-encoded embeddings to generate the pair embedding P. Equations (3)-(5) use Einstein summation notation, where repeated indices that are present only on the right side of the equation are implicitly summed over.

Put another way, the structure prediction system 100 can generate the pair embeddings 118 from the MSA embedding 116 by computing the "outer product mean" of the MSA embedding 116, where the MSA embedding is viewed as an M×N array of embeddings (i.e., where each embedding in the array has dimensionality E). The outer product mean defines a sequence of operations that, when applied to the MSA embedding 116, generates an N×N array of embeddings (i.e., where N is the number of amino acids in the protein) that define the pair embeddings 118.

To compute the outer product mean of the MSA embedding 116, the system 100 can apply an outer product mean operation to the MSA embedding 116, and identify the pair embeddings 118 as the result of the outer product mean operation. To compute the outer product mean, the system generates a tensor A(•), e.g., given by:

$$A(res1, res2, ch1, ch2) = \frac{1}{M} \sum_{m=1...M} LeftAct(m, res1, ch1) \cdot RightAct(m, res2, ch2)$$

where $res1, res2 \in \{1, \ldots, N\}$, where N is the number of amino acids in the protein, $ch1, ch2 \in \{1, \ldots, E\}$, where E is the number of channels in each embedding of the M×N array of embeddings representing the MSA embedding, M is the number rows in the M×N array of embeddings representing the MSA embedding, LeftAct(m, res1, ch1) is a linear operation (e.g., defined by a matrix multiplication) applied to the channel ch1 of the embedding located at the row indexed by "m" and the column indexed by "res1" in the M×N array of embeddings representing the MSA embedding, and RightAct(m, res2, ch2) is a linear operation (e.g., defined by a matrix multiplication) applied to the channel ch2 of the embedding located at the row indexed by "m" and the column indexed by "res2" in the M×N array of embeddings representing the MSA embedding. The result of the outer product mean is generated by flattening and linearly projecting the (ch1, ch2) dimensions of the tensor A. Optionally, the system can perform one or more Layer Normalization operations (e.g., as described with reference to Jimmy Lei Ba et al., "Layer Normalization," arXiv:1607.06450) as part of computing the outer product mean.

Generally, the MSA embedding 116 may be expressed with explicit reference to the multiple amino acid sequences of the MSA 108, e.g., as a 2-D array of embeddings where each row of the 2-D array corresponds to a respective amino acid sequence of the MSA 108. Therefore, the format of the MSA embedding 116 may be inappropriate for predicting the structure 106 of the protein 104, which has no explicit dependence on the individual amino acid sequences of the MSA 108. In contrast, the pair embeddings 118 characterize relationships between respective pairs of amino acids in the protein 104 and are expressed without explicit reference to the multiple amino acid sequences from the MSA 108, and are therefore a more convenient data representation for use in predicting the protein structure 106.

The pair embedding neural network 112 is configured to process the collection of pair embeddings to update the values of the pair embeddings, i.e., to generate updated pair embeddings 120. The pair embedding neural network 112 updates the pair embeddings by processing them using one or more "self-attention" neural network layers. As used throughout this document, a self-attention layer generally refers to a neural network layer that updates a collection of embeddings, i.e., that receives a collection of embeddings and outputs updated embeddings. To update a given embedding, the self-attention layer determines a respective "attention weight" between the given embedding and each of one or more selected embeddings, and then updates the given embedding using: (i) the attention weights, and (ii) the selected embeddings. For convenience, the self-attention layer may be said to update the given embedding using attention "over" the selected embeddings.

In one example, a self-attention layer may receive a collection of input embeddings $\{x_i\}_{i=1}^{N}$, and to update embedding $x_i$, the self-attention layer may determine attention weights $[a_j]_{j \in S_i}$, where $S_i \subset \{1, \ldots, N\}$ and $\alpha_j$ denotes the attention weight between $x_i$ and $x_j$, as:

$$[a_j]_{j \in S_i} = \text{softmax}\left(\frac{(W_q x_i) K_{S_i}^T}{c}\right) \quad (6)$$

$$K_{S_i} = [W_k x_j]_{j \in S_i} \quad (7)$$

where $W_q$ and $W_k$ are learned parameter matrices, softmax(•) denotes a soft-max normalization operation, and c is a constant. Using the attention weights, the self-attention layer may update embedding $x_i$ as:

$$x_i \leftarrow \sum_{j \in S_i} a_j \cdot (W_v x_j) \quad (8)$$

where $W_v$ is a learned parameter matrix.

In addition to the self-attention neural network layers, the pair embedding neural network may include other neural network layers that may be interleaved with the self-attention layers, e.g., linear neural network layers. In one example, the pair embedding neural network 112 has a neural network architecture referred to herein as a "grid transformer neural network architecture," which will be described in more detail with reference to FIG. 2.

The structure prediction system 100 uses the pair embeddings 118 to generate a respective "single" embedding 122 corresponding to each amino acid in the protein 104. In one example, the structure prediction system may generate the single embeddings $S_i$ corresponding to amino acid i as:

$$S_i = \sum_{j=1}^{N} P_{i,j} \quad (9)$$

where $P_{i,j}$ is the pair embedding corresponding to amino acid pair ($A_i$, $A_j$), $A_i$ is the amino acid at position i in the amino acid sequence 102, and $A_j$ is the amino acid at position j in the amino acid sequence 102. In another example, the structure prediction system may further multiply the right-hand-side of equation (9) by a factor of 1/N, i.e., to implement mean pooling rather than sum pooling. In another example, the structure prediction system may identify the single embeddings as the diagonal of the pair embedding matrix, i.e., such that single embedding $S_i$ corresponding to amino acid i is given by $P_{i,i}$, i.e., the pair embedding corresponding to amino acid pair ($A_i$, $A_j$). In another example, prior to processing the pair embeddings 118 using the pair embedding neural network 112, the structure prediction system may have appended an additional row of embeddings to the pair embeddings (where the additional row of embeddings may be initialized with random values or default values). In this example, the collection of pair embeddings may be represented as a matrix with dimensionality (N+1)×N×F, where N is the number of amino acids in the amino acid sequence and F is the dimensionality of each pair embedding. In this example, after processing the pair embeddings using the pair embedding neural network 112, the structure prediction system may extract the appended row of embeddings from the updated pair embeddings 120 and identify the extracted embeddings as the single embeddings 122.

The folding neural network 114 is configured to generate an output specifying the values of structure parameters that define the predicted structure 106 of the protein by processing an input that includes the single embeddings 122, the pair embeddings 120, or both. In one example, the folding neural network 114 may process the single embeddings 122, the pair embeddings 120, or both, using one or more neural network layers, e.g., convolutional or fully-connected neural network layers, to generate an output specifying the values of the structure parameters of the protein 104.

A training engine may train the structure prediction system 100 from end-to-end to optimize a structure loss 126, and optionally, one or more auxiliary losses, e.g., a reconstruction loss 128, a distance prediction loss 130, or both, each of which will be described in more detail next. The training engine may train the structure prediction system 100 on a set of training data including multiple training examples. Each training example may specify: (i) a training input including an amino acid sequence and a corresponding MSA, and (ii) a target protein structure that should be generated by the structure prediction system 100 by processing the training input. Target protein structures used for training the structure prediction system 100 may be determined using experimental techniques, e.g., x-ray crystallography.

The structure loss 126 may characterize a similarity between: (i) a predicted protein structure generated by the structure prediction system 100, and (ii) the target protein structure that should have been generated by the structure prediction system. For example, the structure loss $\mathcal{L}$ structure may be given by:

$$\mathcal{L}_{structure} = \frac{1}{N^2} \sum_{i,j=1}^{N} \left(1 - \frac{|t_{i,j} - \widetilde{t_{i,j}}|}{A}\right)_+ \quad (10)$$

$$t_{ij} = R_i^{-1}(t_j - t_i) \quad (11)$$

$$\widetilde{t_{ij}} = \widetilde{R}_i^{-1}(\widetilde{t_j} - \widetilde{t_i}) \quad (12)$$

where N is the number of amino acids in the protein, $t_i$ denote the predicted location parameters for amino acid i, $R_i$ denotes a 3×3 rotation matrix specified by the predicted rotation parameters for amino acid i, $\widetilde{t_i}$ are the target location parameters for amino acid i, $\widetilde{R}_i$ denotes a 3×3 rotation matrix specified by the target rotation parameters for amino acid i, A is a constant, $R_i^{-1}$ refers to the inverse of the 3×3 rotation matrix specified by predicted rotation parameters $\widetilde{R}_i^{-1}$ refers to the inverse of the 3×3 rotation matrix specified by the target rotation parameters $\widetilde{R}_i$, and $(\cdot)_+$ denotes a rectified linear unit (ReLU) operation.

The structure loss defined with reference to equations (10)-(12) may be understood as averaging the loss $|t_{ij} - \widetilde{t_{ij}}|$ over each pair of amino acids in the protein. The term $t_{ij}$ defines the predicted spatial location of amino acid j in the predicted frame of reference of amino acid i, and $\widetilde{t_{ij}}$ defines the actual spatial location of amino acid j in the actual frame of reference of amino acid i. These terms are sensitive to the predicted and actual rotations of amino acid i and j, and therefore carry richer information than loss terms that are only sensitive to the predicted and actual distances between amino acids. Optimizing the structure loss encourages the structure prediction system 100 to generate predicted protein structures that accurately approximate true protein structures.

The (unsupervised) reconstruction loss 128 measures the accuracy of the structure prediction system 100 in predicting the identities of amino acids from the MSA 108 that were "corrupted" prior to generation of the MSA embedding 116. More specifically, the structure prediction system 100 may corrupt the MSA 108 prior to generation of the MSA embedding 116 by randomly selecting tokens representing the identities of amino acids at particular locations in the MSA 108 to be either modified or masked. The structure prediction system 100 may modify the token representing the identity of an amino acid at a location in the MSA 108 by replacing it with a randomly selected token identifying a different amino acid. The structure prediction system 100 may take into account the frequency with which different amino acids appear in the MSA 108 as part of modifying the tokens identifying the amino acids in the MSA 108. For example, the structure prediction system 100 may generate a probability distribution over the set of possible amino acids, where the probability associated with an amino acid is based on the frequency of occurrence of the amino acid in the MSA 108. The structure prediction system 100 may use the amino acid probability distribution in modifying the MSA 108 by randomly sampling the corrupted amino acid identities in accordance with the probability distribution. The structure prediction system 100 may mask a token representing the identity of an amino acid at a location in the MSA by replacing the token with a specially designated null token.

To evaluate the reconstruction loss 128, the structure prediction system 100 processes the MSA embedding 116, e.g., using a linear neural network layer, to predict the true identity of the amino acid at each corrupted location in the MSA 108. The reconstruction loss 128 may be, e.g., a cross-entropy loss between the predicted and the true identities of the amino acids at the corrupted locations in the MSA 108. The identities of the amino acids at the uncorrupted locations of the MSA 108 may be disregarded during computation of the reconstruction loss 128.

The distance prediction loss 130 measures the accuracy of the structure prediction system 100 in predicting the physical distances between pairs of amino acids in the protein structure. To evaluate the distance prediction loss 130, the structure prediction system 100 processes the pair embeddings 118 generated by the pair embedding neural network 112, e.g., using a linear neural network layer, to generate a distance prediction output. The distance prediction output characterizes the predicted distance between each pair of amino acids in the protein structure 106. In one example, the distance prediction output may specify, for each pair of amino acids in the protein, a probability distribution over a set of possible distance ranges between the pair of amino acids. The set of possible distance ranges may be given by, e.g., {(0,5], (5,10], (10,20], (20,∞)}, where the distances may be measured in Angstroms (or any other appropriate unit of measure). The distance prediction loss 130 may be, e.g., a cross-entropy loss between the predicted and actual distances (ranges) between pairs of amino acids in the protein e.g. between a 1-hot range bin and the ground truth structure. (The distance between a first amino acid and a second amino acid can refer to the distance between a specified atom in the first amino acid a corresponding specified atom in the second amino acid. The specified atom can be, e.g., a carbon alpha atom). In some implementations, the distance prediction output can be understood as defining, or being part of, the structure parameters defining the predicted protein structure 108.

Generally, training the structure prediction system 100 to optimize the auxiliary losses may cause the structure prediction system to generate intermediate representations (e.g., MSA embeddings and pair embeddings) that encode information pertinent to the ultimate goal of protein structure prediction. Therefore, optimizing the auxiliary losses may enable the structure prediction system 100 to predict protein structures with greater accuracy.

The training engine may train the structure prediction system 100 on the training data over multiple training iterations, e.g., using stochastic gradient descent training techniques.

Figure 2:
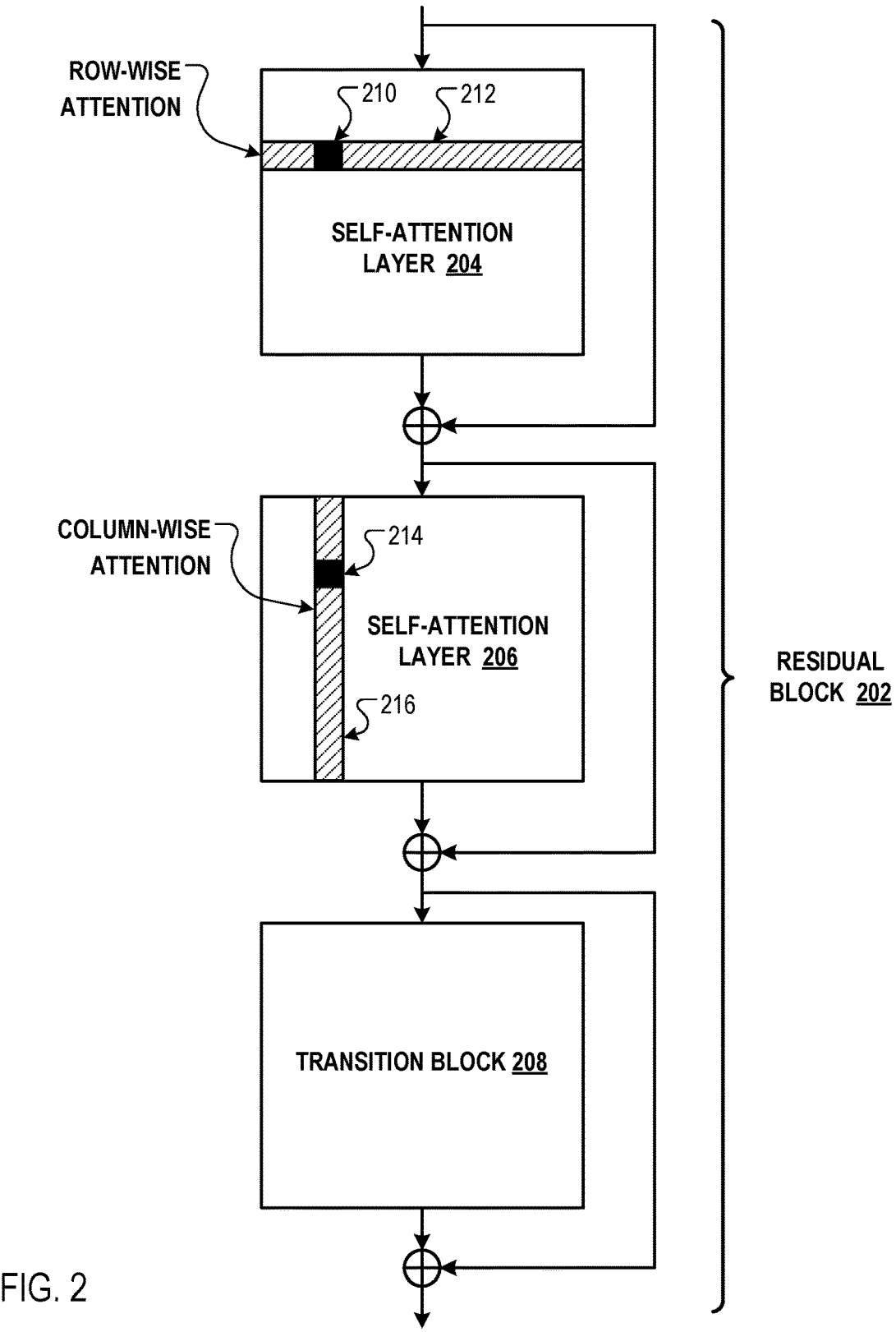
FIG. 2 illustrates an example of a "grid transformer" neural network architecture.

FIG. 2 illustrates an example of a "grid transformer" neural network architecture 200. A grid transformer neural network is configured to receive a collection of embeddings having initial values, to process the collection of embeddings through one or more residual blocks 202, and to output updated values of the collection of embeddings. For convenience, the description that follows will refer to the collection of embeddings being logically organized into a two-dimensional array of embeddings. For example, each embedding may be a pair embedding corresponding to a pair of amino acids in the protein, as described with reference to FIG. 1. In this example, the pair embeddings may be understood as being logically arranged in a two-dimensional array where the embedding at position (i,j) in the array is the pair embedding corresponding to the amino acid pair at positions i and j in the amino acid sequence of the protein. In another example, each embedding may be an embedding of an amino acid from an MSA embedding. In this example, the embeddings may be understood as being logically arranged into a two-dimensional array where the embedding at position (i,j) in the array is the embedding corresponding to the j-th amino acid in the i-th amino acid sequence in the MSA.

Each residual block 202 of the grid transformer architecture includes a self-attention layer 204 that implements "row-wise self-attention," a self-attention layer 206 that implements "column-wise self-attention," and a transition block 208. To reduce computational resource consumption, row-wise and column-wise self-attention layers update each input embedding using attention over only proper subsets of the input embeddings, as will be described in more detail next.

The row-wise self-attention layer 204 updates each embedding using attention over only those embeddings that are in the same row as the embedding in the two-dimensional array of embeddings. For example, the row-wise self-attention layer updates the embedding 210 (i.e., indicated by the darkened square) using attention over the embeddings in the same row (i.e., indicated by the hatched region 212). The residual block 202 may also add the input to the row-wise self-attention layer 204 to the output of the row-wise self-attention layer 204.

The column-wise self-attention layer 206 updates each embedding using attention over only those embeddings that are in the same column as the embedding in the two-dimensional array of embeddings. For example, the column-wise self-attention layer updates the embedding 214 (i.e., indicated by the darkened square) using self-attention over the embeddings in the same column (i.e., indicated by the hatched region 216). The residual block 202 may also add the input to the column-wise self-attention layer to the output of the column-wise self-attention layer.

The transition block 208 may update the embeddings by processing them using one or more linear neural network layers. The residual block 202 may also add the input to the transition block to the output of the transition block.

The grid transformer architecture 200 may include multiple residual blocks. For example, in different implementations, the grid transformer architecture 200 may include 5 residual blocks, 15 residual blocks, or 45 residual blocks.

Figure 3:
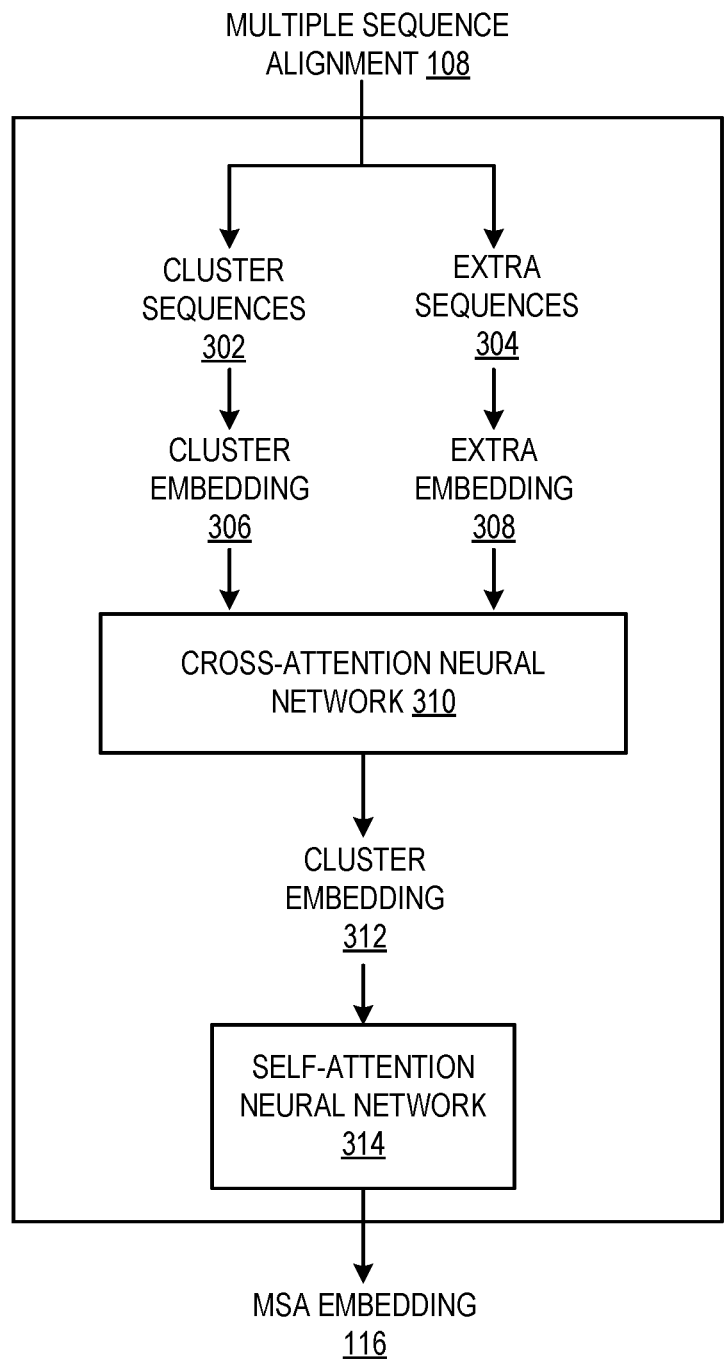
FIG. 3 shows an example multiple sequence alignment (MSA) embedding system.

FIG. 3 shows an example multiple sequence alignment (MSA) embedding system 110. The MSA embedding system 110 is an example of a system implemented as computer programs on one or more computers in one or more locations in which the systems, components, and techniques described below are implemented.

The MSA embedding system 110 is configured to process a multiple sequence alignment (MSA) 108 to generate an MSA embedding 116. Generating an MSA embedding 116 that includes a respective embedding of each amino acid of each amino acid sequence in the MSA 108 may be computationally intensive, e.g., in situations where the MSA includes a large number of lengthy amino acid sequences. Therefore, to reduce computational resource consumption, the MSA embedding system 110 may generate an MSA embedding 116 for only a portion of the amino acid sequences in the entire MSA, referred to as the "cluster sequences" 302.

The MSA embedding system 110 may select the cluster sequences 302 from the MSA 108, e.g., by randomly selecting a predefined number of amino acid sequences from the MSA 108, e.g., 128 or 256 amino acid sequences. The remaining amino acid sequences in the MSA 108 that are not selected as cluster sequences 302 will be referred to herein as "extra sequences" 304. Generally, the number of cluster sequences 302 is chosen to be substantially less than the number of extra sequences 304, e.g., the number of cluster sequences 302 may be an order of magnitude less than the number of extra sequences 304.

The MSA embedding system 110 may generate a cluster embedding 306 of the cluster sequences 302 and an extra embedding 308 of the extra sequences 304, e.g., using the technique described above with reference to equation (1).

The MSA embedding system 110 may then process the cluster embedding 306 and the extra embedding 308 using a cross-attention neural network 310 to generate an updated cluster embedding 312. The cross-attention neural network 310 includes one or more cross-attention neural network layers. A cross-attention neural network layer receives two separate collections of embeddings, one of which may be designated as "variable" and the other as "static," and updates one (the variable) collection of embeddings using attention over the other (static) collection of embeddings. That is, the cross-attention layer may be understood as updating the variable collection of embeddings with information drawn from the static collection of embeddings.

In one example, the cross-attention neural network 310 may include a sequence of residual blocks, where each residual block includes two cross-attention layers and a transition block. The first cross-attention layer may receive the cluster embeddings 306 as the variable collection of embeddings and the extra embeddings 308 as the static collection of embeddings, and thereafter update the cluster embeddings 306 with information from the extra embeddings 308. The second cross-attention layer may receive the extra embeddings 308 as the variable collection of embeddings and the cluster embeddings 306 as the static collection of embeddings, and thereafter update the extra embeddings 308 with information from the cluster embeddings 306. Each residual block may further include a transition block after the second cross-attention layer that updates the cluster embeddings using one or more linear neural network layers. For both cross-attention layers and the transition block, the residual block may add the input to the layer/block to the output of the layer/block.

In some cases, to improve computational efficiency, the cross-attention layers may implement a form of "global" cross-attention by determining a respective attention weight for each amino acid sequence (e.g., in the cluster or extra sequences), i.e., rather than a respective attention weight for every amino acid. In these cases, each amino acid in an amino acid sequence shares the same attention weight as the amino acid sequence.

The cross-attention neural network 310 may be understood as enriching the cluster embedding 306 with information from the extra embedding 308 (and vice-versa). After the completion of the operations performed by the cross-attention neural network 310, the extra embedding 308 is discarded, and only the cluster embedding 312 is used in generating the MSA embedding 116.

The MSA embedding system 110 generates the MSA embedding 116 by processing the cluster embeddings 312 using a self-attention neural network 314, e.g., having the grid transformer architecture described with reference to FIG. 2. Processing the cluster embeddings 312 using the self-attention neural network 314 may enhance the cluster embedding by "sharing" information among embeddings within and between cluster sequences.

The MSA embedding system 110 may provide the output of the self-attention neural network 314 (i.e., corresponding to the updated cluster embedding 306) as the MSA embedding 116.

Figure 4:
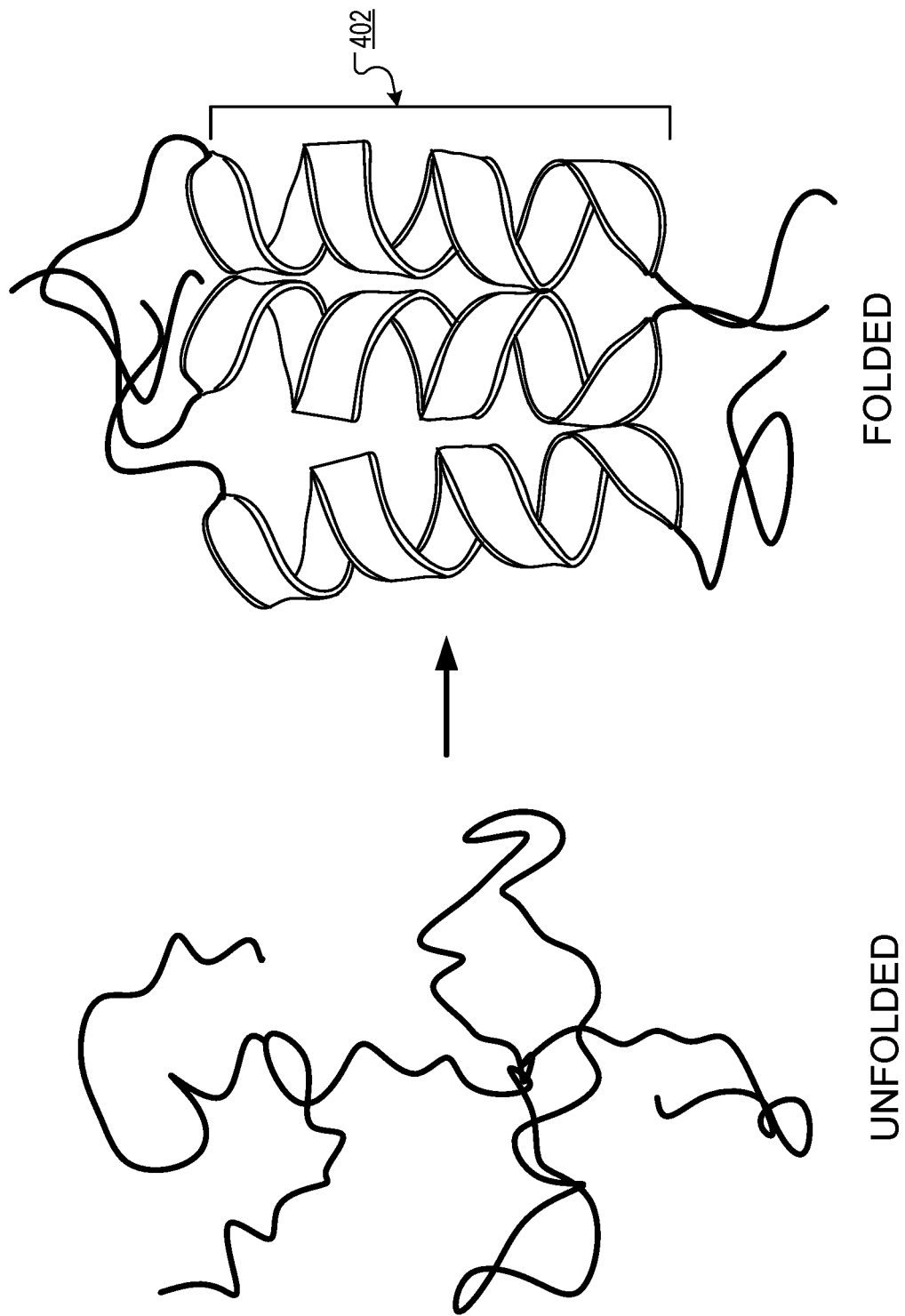
FIG. 4 is an illustration of an unfolded protein and a folded protein.

FIG. 4 is an illustration of an unfolded protein and a folded protein. The unfolded protein is a random coil of amino acids. The unfolded protein undergoes protein folding and folds into a 3D configuration. Protein structures often include stable local folding patterns such alpha helices (e.g., as depicted by 402) and beta sheets.

Figure 5:
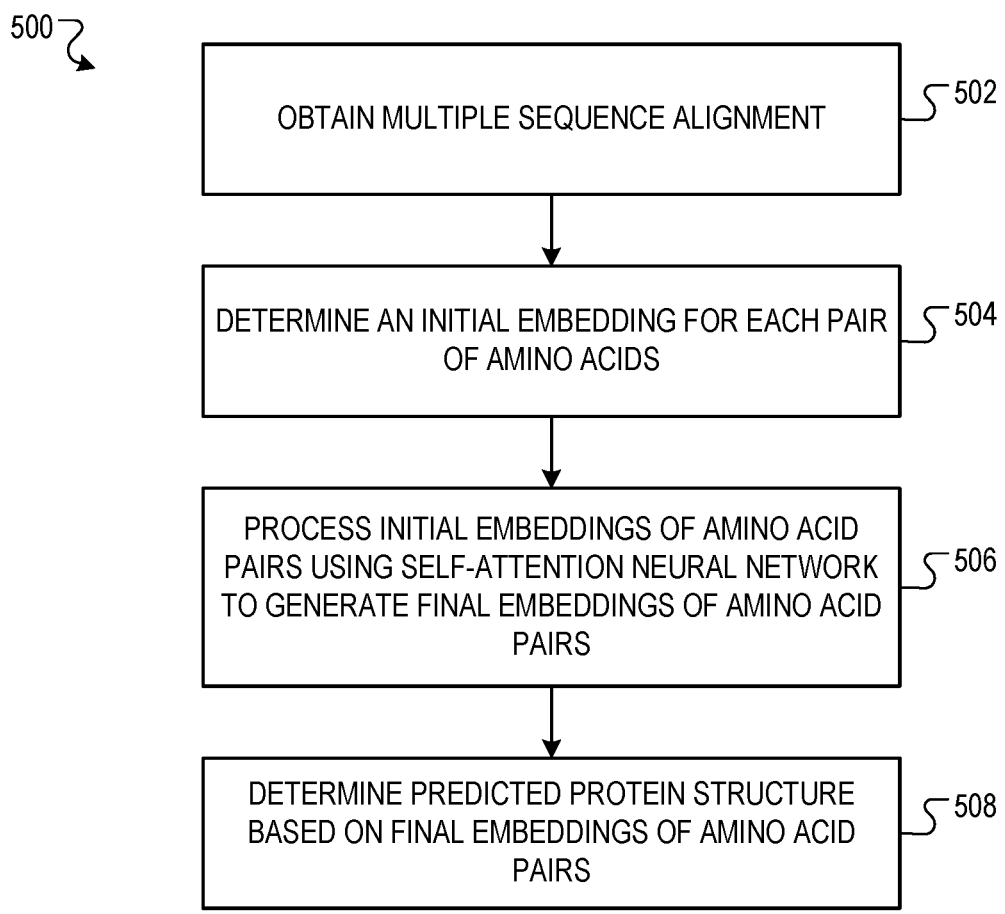
FIG. 5 is a flow diagram of an example process for determining a predicted protein structure.

FIG. 5 is a flow diagram of an example process 500 for determining a predicted protein structure. For convenience, the process 500 will be described as being performed by a system of one or more computers located in one or more locations. For example, a protein structure prediction system, e.g., the protein structure prediction system 100 of FIG. 1, appropriately programmed in accordance with this specification, can perform the process 500.

The system obtains a multiple sequence alignment for the amino acid sequence specifying the protein (502).

The system processes the multiple sequence alignment to determine a respective initial embedding for each pair of amino acids in the amino acid sequence of the protein (504).

The system processes the initial embeddings of the pairs of amino acids using a pair embedding neural network that includes multiple self-attention neural network layers to generate a final embedding of each pair of amino acids (506). Each self-attention layer of the pair embedding neural network may be configured to: (i) receive a current embedding of each pair of amino acids, and (ii) update the current embedding of each pair of amino acids using attention over the current embeddings of the pairs of amino acids. In some cases, the self-attention layers of the pair embedding neural network may alternate between row-wise self-attention layers and column-wise self-attention layers.

The system determines the predicted structure of the protein based on the final embedding of each pair of amino acids (508). For example, the system may process the final embeddings of the amino acid pairs to generate a respective "single" embedding for each amino acid in the protein, and process the single embeddings using a folding neural network to determine the predicted structure of the protein.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers for determining a predicted three-dimensional structure of a protein that is specified by an amino acid sequence, the method comprising:
   obtaining a multiple sequence alignment for the protein, wherein multiple sequence alignment defines a sequence alignment of the amino acid sequence of the protein with a respective amino acid sequence of each of a plurality of homologous proteins;
   determining, from the multiple sequence alignment and for each pair of amino acids in the amino acid sequence of the protein, a respective initial embedding of the pair of amino acids;
   processing the initial embeddings of the pairs of amino acids using a pair embedding neural network comprising a plurality of self-attention neural network layers to generate a final embedding of each pair of amino acids; and
   determining the predicted three-dimensional structure of the protein based on the final embedding of each pair of amino acids.

2. The method of claim 1, wherein each self-attention neural network layer of the pair embedding neural network is configured to perform operations comprising:
   receiving a current embedding of each pair of amino acids; and
   updating the current embedding of each pair of amino acids using attention over the current embeddings of the pairs of amino acids.

3. The method of claim 2, wherein for each pair of amino acids, updating the current embedding of the pair of amino acids using attention over the current embeddings of the pairs of amino acids comprises:
   updating the current embedding of the pair of amino acids using attention over only a proper subset of the current embeddings of the pairs of amino acids.

4. The method of claim 3, wherein:
   one or more of the self-attention neural network layers are row-wise self-attention neural network layers; and
   for each row-wise self-attention neural network layer, updating the current embedding of the pair of amino acids using attention over only a proper subset of the current embeddings of the pairs of amino acids comprises:
     updating the current embedding of the pair of amino acids using attention over only current embeddings of pairs of amino acids that are located in a same row as the current embedding of the pair of amino acids in an arrangement of the current embeddings of the pairs of amino acids into a two-dimensional array.

5. The method of claim 4, wherein:
   one or more of the self-attention neural network layers are column-wise self-attention neural network layers; and for each column-wise self-attention neural network layer, updating the current embedding of the pair of amino acids using attention over only a proper subset of the current embeddings of the pairs of amino acids comprises:
updating the current embedding of the pair of amino acids using attention over only current embeddings of pairs of amino acids that are located in a same column as the current embedding of the pair of amino acids in the arrangement of the current embeddings of the pairs of amino acids into the two-dimensional array.

6. The method of claim 5, wherein the plurality of self-attention neural network layers of the pair embedding neural network comprise an alternating sequence of row-wise self-attention neural network layers and column-wise self-attention neural network layers.

7. The method of claim 1, wherein determining the predicted structure of the protein based on the final embedding of each pair of amino acids comprises:
determining a respective initial embedding of each amino acid in the amino acid sequence of the protein based on the final embeddings of the pairs of amino acids; and
determining the predicted structure of the protein based on the initial embedding of each amino acid in the amino acid sequence.

8. The method of claim 1, wherein determining, from the multiple sequence alignment and for each pair of amino acids in the amino acid sequence of the protein, a respective initial embedding of the pair of amino acids comprises:
partitioning the multiple sequence alignment into: (i) a set of cluster amino acid sequences, and (ii) a set of extra amino acid sequences;
generating: (i) an embedding of the set of cluster amino acid sequences, and (ii) an embedding of the set of extra amino acid sequences;
processing a network input comprising: (i) the embedding of the cluster amino acid sequences, and (ii) the embedding of the extra amino acid sequences, using a cross-attention neural network to update the embedding of the cluster amino acid sequences; and
determining the initial embeddings of the pairs of amino acids based on the updated embedding of the cluster amino acid sequences.

9. The method of claim 8, wherein processing a network input comprising: (i) the embedding of the cluster amino acid sequences, and (ii) the embedding of the extra amino acid sequences, using a cross-attention neural network to update the embedding of the cluster amino acid sequences comprises repeatedly performing operations including:
updating the embedding of the cluster amino acid sequences using attention over the embedding of the extra amino acid sequences; and
updating the embedding of the extra amino acid sequences using attention over the embedding of the cluster amino acid sequences.

10. A system comprising:
one or more computers; and
one or more storage devices communicatively coupled to the one or more computers, wherein the one or more storage devices store instructions that, when executed by the one or more computers, cause the one or more computers to perform operations for determining a predicted three-dimensional structure of a protein that is specified by an amino acid sequence, the operations comprising:

obtaining a multiple sequence alignment for the protein, wherein multiple sequence alignment defines a sequence alignment of the amino acid sequence of the protein with a respective amino acid sequence of each of a plurality of homologous proteins;
determining, from the multiple sequence alignment and for each pair of amino acids in the amino acid sequence of the protein, a respective initial embedding of the pair of amino acids;
processing the initial embeddings of the pairs of amino acids using a pair embedding neural network comprising a plurality of self-attention neural network layers to generate a final embedding of each pair of amino acids; and
determining the predicted three-dimensional structure of the protein based on the final embedding of each pair of amino acids.

11. The system of claim 10, wherein each self-attention neural network layer of the pair embedding neural network is configured to perform operations comprising:
receiving a current embedding of each pair of amino acids; and
updating the current embedding of each pair of amino acids using attention over the current embeddings of the pairs of amino acids.

12. The system of claim 11, wherein for each pair of amino acids, updating the current embedding of the pair of amino acids using attention over the current embeddings of the pairs of amino acids comprises:
updating the current embedding of the pair of amino acids using attention over only a proper subset of the current embeddings of the pairs of amino acids.

13. The system of claim 12, wherein:
one or more of the self-attention neural network layers are row-wise self-attention neural network layers; and
for each row-wise self-attention neural network layer, updating the current embedding of the pair of amino acids using attention over only a proper subset of the current embeddings of the pairs of amino acids comprises:
updating the current embedding of the pair of amino acids using attention over only current embeddings of pairs of amino acids that are located in a same row as the current embedding of the pair of amino acids in an arrangement of the current embeddings of the pairs of amino acids into a two-dimensional array.

14. The system of claim 13, wherein:
one or more of the self-attention neural network layers are column-wise self-attention neural network layers; and
for each column-wise self-attention neural network layer, updating the current embedding of the pair of amino acids using attention over only a proper subset of the current embeddings of the pairs of amino acids comprises:
updating the current embedding of the pair of amino acids using attention over only current embeddings of pairs of amino acids that are located in a same column as the current embedding of the pair of amino acids in the arrangement of the current embeddings of the pairs of amino acids into the two-dimensional array.

15. The system of claim 14, wherein the plurality of self-attention neural network layers of the pair embedding neural network comprise an alternating sequence of row-wise self-attention neural network layers and column-wise self-attention neural network layers.

16. One or more non-transitory computer storage media storing instructions that when executed by one or more computers cause the one or more computers to perform operations for determining a predicted three-dimensional structure of a protein that is specified by an amino acid sequence, the operations comprising:
- obtaining a multiple sequence alignment for the protein, wherein multiple sequence alignment defines a sequence alignment of the amino acid sequence of the protein with a respective amino acid sequence of each of a plurality of homologous proteins;
- determining, from the multiple sequence alignment and for each pair of amino acids in the amino acid sequence of the protein, a respective initial embedding of the pair of amino acids;
- processing the initial embeddings of the pairs of amino acids using a pair embedding neural network comprising a plurality of self-attention neural network layers to generate a final embedding of each pair of amino acids; and
- determining the predicted three-dimensional structure of the protein based on the final embedding of each pair of amino acids.

17. The non-transitory computer storage media of claim 16, wherein each self-attention neural network layer of the pair embedding neural network is configured to perform operations comprising:
- receiving a current embedding of each pair of amino acids; and
- updating the current embedding of each pair of amino acids using attention over the current embeddings of the pairs of amino acids.

18. The non-transitory computer storage media of claim 17, wherein for each pair of amino acids, updating the current embedding of the pair of amino acids using attention over the current embeddings of the pairs of amino acids comprises:
- updating the current embedding of the pair of amino acids using attention over only a proper subset of the current embeddings of the pairs of amino acids.

19. The non-transitory computer storage media of claim 18, wherein:
- one or more of the self-attention neural network layers are row-wise self-attention neural network layers; and
- for each row-wise self-attention neural network layer, updating the current embedding of the pair of amino acids using attention over only a proper subset of the current embeddings of the pairs of amino acids comprises:
- updating the current embedding of the pair of amino acids using attention over only current embeddings of pairs of amino acids that are located in a same row as the current embedding of the pair of amino acids in an arrangement of the current embeddings of the pairs of amino acids into a two-dimensional array.

20. The non-transitory computer storage media of claim 19, wherein:
- one or more of the self-attention neural network layers are column-wise self-attention neural network layers; and
- for each column-wise self-attention neural network layer, updating the current embedding of the pair of amino acids using attention over only a proper subset of the current embeddings of the pairs of amino acids comprises:
- updating the current embedding of the pair of amino acids using attention over only current embeddings of pairs of amino acids that are located in a same column as the current embedding of the pair of amino acids in the arrangement of the current embeddings of the pairs of amino acids into the two-dimensional array.

* * * * *